United States Patent [19]

Rossini et al.

[11] Patent Number: 5,026,365
[45] Date of Patent: Jun. 25, 1991

[54] METHOD AND APPARATUS FOR THERAPEUTICALLY TREATING IMMUNOLOGICAL DISORDERS AND DISEASE STATES

[75] Inventors: Aldo A. Rossini, Sudbury; John P. Mordes, Waban; Eugene S. Handler, West Newton, all of Mass.

[73] Assignee: The University of Massachusetts, Boston, Mass.

[21] Appl. No.: 43,934

[22] Filed: Apr. 29, 1987

[51] Int. Cl.$^5$ ...................... A61K 9/22; A01N 93/00
[52] U.S. Cl. ................................ 604/891.1; 424/93; 514/866
[58] Field of Search ................... 604/891.1, 890.1, 27, 604/28, 93; 623/11; 424/422–424, 83; 514/866, 885

[56] References Cited

U.S. PATENT DOCUMENTS

| 4,352,883 | 10/1982 | Lim | 623/11 |
| 4,353,888 | 10/1982 | Sefton | 623/11 |
| 4,364,385 | 12/1982 | Lossef | 604/27 |
| 4,391,909 | 7/1983 | Lim | 623/11 |
| 4,686,098 | 8/1987 | Kopchick et al. | 424/424 |

FOREIGN PATENT DOCUMENTS 0213908  3/1987  European Pat. Off. .............. 623/11

OTHER PUBLICATIONS

Rossini et al., "Science", vol. 219, pp. 975–977, 2-25-83.
Sun et al., "Diabetes", vol. 26, No. 12, Dec. 1977.
Davis, K. C., Hayward, A., Ozturk, G., et al., Lymphocyte Transfusion in a Case of Acquired Immunodeficiency Syndrome, Lancet 1:599–600 (1983).
Petrakis, N. L.; Davis, M.; Lucia, S. P.: The In Vivo Differentiation of Human Leukocytes into Histiocytes, Fibroblasts and Fat Cells in Subcutaneous Diffusion Chambers, Blood 17: 109–118 (1961).
Greenberger, J. S.; Hassan, L. R.; Karpas, A.; France, D. S.; Moloney, W. C. Leucocyte Alkaline Phosphatase Elevation in Human Acute Leukaemia Derived Cell Lines Cultured in Diffusion Chambers, Scand. J. Haematol. 19: 242–254 (1977).
AIDS, Annals of the New York Academy of Sciences, vol. 437, pp. 312, 313, 326, 999, 1000, 1010, 1984.
Rossini et al., J. Clin. Invest. 74: 39–44 (1984).
Rossini et al., Ann. Rev. Immunol. 3:289–329 (1985).
Baratano et al., Diabetol. 19:255 (1980).
Zier et al., Diabetes 33:552 (1984).
Hunag & McClaren, Science 192:64 (1976).
Chappel et al., Metabolism 32 (Suppl. I):8 (1983).
Yale & Marliss, Clin. Exp. Immunol. 57:1–20 (1984).
Fauci et al., Ann. Int. Med. 102:800–813 (1985).
Fauci et al., Ann. Int. Med. 106:421–433 (1987).
Science 224:500–503 (1984).
Lane et al., N. Engl. J. Med. 311:1099–1103 (1984).
Carsten, A. L., Bibl. Haemat. 48:321–365 (1984).

Primary Examiner—C. Fred Rosenbaum
Assistant Examiner—Sharon Rose
Attorney, Agent, or Firm—Hamilton, Brook, Smith & Reynolds

[57] ABSTRACT

A unique method and apparatus for therapeutically treating immunological disorders and disease states which are characterized by the present of immunologically abnormal leukocytes in the body of the afflicted subject is provided. The apparatus and methodology utilized a sealed diffusion chamber which may be surgically implanted in-vivo or may be extracorporeally joined to the circulatory system of the afflicted subject. In either mode of use, the diffusion chamber utilizes immunologically normal leukocytes of various types and concentration which are able to provide cell functions and cellular secretory products which therapeutically counterbalance the effects of the immunological abnormality within the afflicted subject.

12 Claims, 4 Drawing Sheets

METHOD AND APPARATUS FOR THERAPEUTICALLY TREATING IMMUNOLOGICAL DISORDERS AND DISEASE STATES

BACKGROUND OF THE INVENTION

The present invention is concerned with the pathology of autoimmune diseases and is particularly concerned with therapeutic treatments for immunological disorders and disease states which are characterized by functionally abnormal white blood cells, leukocytes, in the body of an afflicted subject.

FIELD OF THE INVENTION

It is generally recognized and accepted that autoimmune diseases and pathological states are not the result of a single causative agent or a solitary mechanism of action. Small amounts of auto-antibody and/or lymphocytes directed against a specific target are normally produced in the afflicted individual and are believed to play pathophysiological roles in cellular interactions throughout the course of the disease or disorder. In many instances, there are observable defects in the helper and/or suppressor lymphocyte functions of the white blood cells—a condition which has been categorized as cell-mediated autoimmunity.

Certain autoimmune diseases which are at least partially cell-mediated comprise those immunological disorders and disease states in which leukocytes, most notably T-cell lymphocytes, have become specifically activated by, directed against, and destructive of autologous tissues. Cytotoxic or killer T-cell lymphocytes generated by this aberrant immune response attack and injure specific organs, sometimes in the total absence of observable serum auto-antibodies. A diminished suppressor T-cell activity is believed to result in disordered regulation of immune responses and to allow overactivity of other autoreactive mechanisms, all of which involve functionally abnormal white blood cells circulating within the body of the afflicted subject.

In describing an overview of cell-mediated immunological disorders and disease states, it is useful to recognize those clinical conditions for which there is an identifiable causative agent and to distinguish these from those pathological states for which no specific cause has yet been demonstrated. This is best illustrated by a summary of two different cell-mediated clinical disorders: human insulin-dependent diabetes mellitus (hereinafter "IDDM"); and acquired immunodeficiency syndrome (hereinafter "AIDS").

Insulin-Dependent Biabetes Mellitus (IDDM)

Insulin-dependent diabetes mellitus (IDDM) is a pathological disorder in which the body's own lymphocytes destroy the insulin producing beta cells located in the pancreas At this time, there are close to one million individuals afflicted with IDDM living in the United States. Those affected are dependent upon injections of insulin for the rest of their lives. Insulin therapy now prevents the early deaths from ketoacidosis that were formerly inevitable; and has substantially extended the life expectancy of these people. Insulin treatment, however, does not prevent the later complications of chronic diabetes. These complications include diseases of the heart, kidneys, eyes, and the nervous system. The life expectancy for an individual developing diabetes at age 14 is all too often less than 25 or 30 years. At this time, there is no generally accepted, safe way to prevent the disease or reverse it once the pathology has begun.

The cause of IDDM is unknown. While there is evidence to support involvement of viral illness in some instances, most contemporary data indicate that an immunological disorder which is at least partially cell-mediated is involved [Rossini et al., *Ann. Rev. Immunol.* 3:289-329 (1985)]. Morphologically, "Insulitis" defined as an inflammation surrounding the insulin producing beta cells of the pancreas is often found at the time of disease onset. Abnormalities of both the cellular and humoral components of the immune system are present. For example, islet cell cytoplasmic antibodies and islet cell surface antibodies are found at the time of clinical diagnosis in children and have been detected in some individuals long before the onset of the clinical symptoms. Cellular immune functions are also altered. Activated T-cell lymphocytes capable of cytotoxic function normally, circulate in increased numbers in instances of acute IDDM. Defects in suppressor cell activity and alterations in the production of lymphokines such as Interferon and Interleukin-2 have been reported in diabetic children [Baratano et al., *Diabetol.* 19:255 (1980); Zier et al., *Diabetes* 33:552 (1984)]. Lymphocytes from acutely diabetic children that are co-cultured with human beta cells (from an insulinproducing tumor) are reported to have killed the tumor cells [Huang and McClaren, *Science* 192:64 (1976)]. In addition, it is now recognized that immunosuppressive therapy using cyclosporine can ameliorate IDDM if the drug is given at the time of disease onset. Unfortunately, lifelong drug treatment may be necessary in order to prevent recurrence of diabetes. There is also the risk of serious long-lasting immune system alterations caused by long term immunosuppressive therapy such that the therapeutic regimen could have consequences worse than those of the disease.

Recent research has utilized animal test model systems which are directly comparable to human IDDM. To date, the best analogue of human IDDM is provided by the BB rat [Chappel et al., *Metabolism* 32 (Suppl. I):8 (1983)]. Inheritable diabetes in the BB rat is characterized by many metabolic, pathologic, and immunologic features directly analogous to those observed in human IDDM [Rossini et al., *Ann. Rev. Immunol.* 3:289-320 (1985); Yale and Marliss, *Clin. Exp. Immunol.* 57:1-20 (1984)]. Functional abnormalities of cellular immunity have been well documented. Mitogen stimulated spleen cells from acutely diabetic rats adoptively transfer both insulitis and diabetes to various recipient rats. Marked lymphopenia involving all lymphocyte subsets occurs consistently in the BB rat. Activated T-lymphocytes have been reported during the early stages of clinical diabetes and to decrease over time with the course of the disease. The responsiveness of BB lymphocytes to mitogens is defective and lymphocytic thyroiditis also occurs in these rats. In addition, abnormal humoral immune regulation in the BB rat is suggested by the presence of islet cell surface antigens and auto-antibodies against thyroid, gastric parietal cells, splenic lymphocytes, and smooth muscle. Lastly, it has been demonstrated that islets from resistant BB rats transplanted to spontaneously diabetic rats are rapidly destroyed.

Recently, it has been demonstrated that weekly transfusions of whole blood from nondiabetic rats to susceptible rats reduced the incidence of diabetes and the incidence of pancreatic insulitis [Rossini et al., *Science*

219:975-977 (1983)]; and that transfusions of lymphocytes from diabetes resistant rats to diabetes prone BB rats prevent onset of the clinical disease in essentially all recipients [Rossini et al., *J. Clin. Invest.* 74:39-44 (1984)]. It is noted that such transfusions not only prevent diabetes, but also restore the depressed mitogenic responsiveness of BB rat lymphocytes.

The recognized difficulty in a therapeutic treatment based on the transfer of white blood cells from a normal to an afflicted subject lies in the histoincompatibility of the transferred cells themselves within the host. Clearly, the HLA antigens of the Major Histocompatibility Complex must be shared between the donor cells and the recipient tissues. Also unknown is the duration and degree of effectiveness which could be achieved by such a direct transfer of donor white blood cells to a subject afflicted with IDDM.

Acquired Immunodeficiency Syndrome (AIDS)

No disease in recent history has preoccupied the medical community or provoked public concern as has AIDS. As of December, 1985, 15,800 patients meeting the reports in 1981, the number of cases reported each half-year has increased. Over 5,000 patients are known to have died (49% of adults and 69% of children); and 75% of patients diagnosed before January, 1983, had died by April, 1985 [*Morbid. Mortal.* 34:245-248 (1985)]. The syndrome is characterized by the destruction of lymphoid cells required for the normal function of the body's immune system [Fauci, A., *Ann. Int. Med.* 102:800-813 (1985)]. Because of this immunodeficiency, subjects with AIDS are found to develop unusual malignancies (such as Kaposi's sarcoma) as well as unusual, often fatal infections, by opportunistic pathogens (such as *Pneumocystis carinii* pneumonia). It is now generally recognized that the acquired immunodeficiency syndrome is caused by a human T-lymphotrophic retrovirus designated HTLV-III [*Science* 224:500-503 (1984)].

To date, there is no effective therapy for the acquired immunodeficiency syndrome. Therapeutic interventions have generally followed one of two directions: attempts to destroy the causative virus; and attempts to overcome the virus-induced immune disorder. While neither tactic has yet produced useful results, a number of immunological approaches to treatment have been attempted. These include: the use of Interleukin-2 (IL-2) to enhance cytotoxic lymphocyte function; the use of gamma-Interferon to boost monocyte and macrophage cytotoxicity [Fauci et al., *Ann. Int. Med.* 106:421-433 (1987)]; and immune reconstitution through the adoptive transfer of lymphocytes or bone marrow [Lane et al., *N. Engl. J. Med.* 311:1099-1103 (1984)]. While none of these approaches have produced enduring clinical benefits, some have been able to temporarily alter the observed functional abnormalities of the leukocytes in the afflicted subject. This is best demonstrated in the Lane study of cellular reconstitution in which lymphocytes and bone marrow from an identical twin 24 to a patient with AIDS resulted in a rise in helper/inducer T-cell numbers and the development of a substantial delayed-type hypersensitivity reaction. No enduring clinical benefit was obtained however, presumably because of the destruction of the transferred normal cells by the HTLV-III virus in the subject. It thus appears clear that attempts at immunological reconstitution will be of minimal, temporary value so long as the causative virus remains viable in the subject; the transient presence of normal cells is demonstratably insufficient to lead to the destruction of the causative virus or initiate reversal of the immunological disorder and disease state incurred as a consequence of the immunologically abnormal leukocytes.

From these summaries of IDDM and AIDS, each of which represents those immunological disorders and disease states which are at least partially cell-mediated, it is apparent that there remains a continuing and vital need for apparatus and therapeutic methods: which are functional when a specific causative agent is present in the afflicted subject; which can be used when there is no apparent or specific cause; which can be utilized and be regulated to meet specific differences among the various clinical disorders and pathological disease states; and which provide benefits in-vivo to the afflicted subject such as are conferred immunologically by normal and functional leukocytes from healthy donors. Novel therapeutic regimens and apparatus able to provide these benefits would be generally recognized as major advances and improvements in this art.

SUMMARY OF THE INVENTION

The present invention is a method for therapeutically treating immunological disorders and disease states which are characterized by the presence of immunologically abnormal leukocytes in the body of an afflicted subject, the method comprising the steps of: obtaining a sealed diffusion chamber of definable configuration and internal volume comprising at least one semi-permeable membrane and a suspension of immunologically normal leukocytes, the semi-permeable membrane retaining the leukocyte suspension within the diffusion chamber while allowing non-cellular materials and fluids to pass therethrough, the leukocytes in the suspension being demonstratably able to provide such cell functions and secretory products which therapeutically counterbalance the effects of the immunological abnormality within the afflicted subject; and implanting the sealed diffusion chamber at a preselected site within the afflicted subject. Alternatively, the sealed diffusion chamber can be extracorporeally joined to the circulatory system of the afflicted subject. It is preferred that the suspension of leukocytes within the diffusion chamber be adult, pre-stimulated leukocytes of determinable type and preferably include specific T-cell populations from cloned cell lines or cells from human donors which have been enriched prior to use.

DETAILED DESCRIPTION OF THE FIGURES

The present invention can be more completely and easily understood when taken in conjunction with the accompanying drawing, in which.

DETAILED DESCRIPTION OF THE PREFERRED EMBODIMENTS

Figure 2:
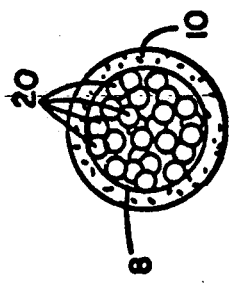
FIG. 2 is a cross-sectional view of the embodiment illustrated within FIG. 1.

The present invention is a methodology which utilizes specific apparatus for therapeutically treating a variety of autoimmune diseases and disorders which are often partially cell-mediated. These immunological disorders and pathological disease states are always characterized by the presence of functionally abnormal white blood cells within the body of the afflicted subject. The present invention is based upon the unique recognition and finding that the clinically observable conditions and symptoms of such immunological disorders and disease states can be counterbalanced by the presence of immunologically and functionally normal white blood cells—which, after interaction, are able to release a variety of different secretory products which aid in the regulation of the immune system; can prevent the onset of the clinical disease; and, in some instances, restore normal function to the injured tissues and organs within the afflicted subject. The present methodology provides for a segregated transfusion of normal leukocytes which interact within a sealed diffusion chamber to release secretory products and soluble factors which function as chemical mediators to counterbalance the effects and pathology of the disease or disorder.

Initially, it must be recognized that not all autoimmune disease states are cell-mediated disorders in which immunologically abnormal, functionally deficient, non-antibody producing cells are clinically observable within 5 the afflicted subject. Clearly, disorders involving B-lymphocytes and their direct precursor cells are not within this class of immunological disorder and disease. Similarly, several autoimmune diseases are recognized as being caused by humoral auto-antibody in the absence of cell-mediated autoimmunity. Representative examples of humoral antibody-mediated autoimmunity include hemolytic anemias, idiopathic thrombocytopenia, and Goodpasture's syndrome, all of which are presently believed to be mediated solely by auto-antibodies directed against autologous cell membrane constituents. In these diseases, it is the antibody which attaches to the cell membranes; fixes complement; and causes severe injury to the cell. Alternatively, antireceptor auto-antibodies are believed to either stimulate or suppress target cell function.

In comparison, those immunological disorders and disease states which are cell mediated typically present immunofunctionally abnormal leukocytes whose characteristics include some or all of the following: a poor or totally absent response to mitogens such as Concanavalin A (hereinafter "CON A"); a diminished or total inability to produce lymphokines or other soluble cytokinetic secretory products such as interleukins and interferons; an impaired ability to react to foreign-antigens by mixed lymphocyte reaction; a reduced delayed-type hypersensitivity reaction; identifiable alterations and changes in cell activation and formation of cytotoxic cells; a reduced or altered ability to aid those cells directly involved in immunoglobulin synthesis or antigen processing for antibody production; an altered or diminished ability to synthesize polypeptides and proteins; an inability to release secretory products normally obtained from the cell; and/or an altered HLA or MHC cell specificity or type.

The present invention is therapeutically effective for those immunological disorders and diseases in which the leukocytes in the body of the subject demonstrate one or more of these immunofunctional abnormalities or immunologically deficient characteristics identified above. The presence of such functionally abnormal or deficient white blood cells circulating within the afflicted subject identifies that pathological state to be one susceptible to treatment using the present invention.

A representative, but incomplete, listing of clinical disorders amenable to treatment using the method and apparatus of the present invention include the following: diabetes mellitus—an affliction in which there is a demonstrated deficiency in the production of Interleukin-2 (hereinafter "IL-2"), a secretory product of lymphocytes; AIDS—a disease in which a functional deficiency of CED4+ helper T-cells has been found and in which there is a decreased production of lymphokines; multiple sclerosis in which alterations in helper and suppressor T-cells have been observed; rheumatoid arthritis—cell mediated destruction of synorium; Addison's disease—cell mediated destruction of adrenals; vasculitis; progressive multifocal leukoencephalopathy; thymic hypoplasia (DiGeorge's syndrome); Wiscott-Aldrich syndrome; Grave's disease; ankylosing spondylitis; and secondary, cell-mediated immunodeficiencies associated with sarcoidosis and Hodgkin's disease. It will be recognized and appreciated that many other immunological disorders and disease states which are at least partially cell-mediated can be therapeutically treated by the present invention to counterbalance the effects of the immunological abnormality within the afflicted subject.

In this regard, the term "to counterbalance" as used herein will be recognized and understood to be employed in its most general connotation and application, and includes the more specific conditions of: "to compensate"—that is, to be equivalent to or to supply an equivalent; "to counteract"—that is, to make an effective or to mitigate the ill effects of; "to neutralize"—that is, to nullify or destroy the effect of; "to control"—that is, to regulate or to exercise a restraining or directing influence over; and "to reverse"—that is, to turnabout or place in opposite direction. Clearly, the term "counterbalance" and the counterbalancing effect of the invention will thus vary with the particular affliction; the degree of injury to the cells, tissues, and organs of the subject already incurred; and the progression of the pathological state for the specific disorder. While the entire range of remedial conditions and benefits may be obtainable in one individual under certain instances, it is expected and envisioned that a broad range of corrective reactions leading to a complete remission or cure of the disorder is not likely using the present invention alone. For this reason, it is expected that the methods and apparatus described herein will comprise but one part of an overall therapeutic regimen which includes conventional pharmaceuticals and drugs and other therapeutic treatments.

The methods of the present invention utilize surgically implantable diffusion chambers or extracorporeal diffusion chambers of a definable configuration and internal volume. A wide variety of diffusion chambers for in-vivo use of various construction, materials, sizes, and internal volumes are conventionally known [Carsten, A. L., *Bibl. Haemat.* 48:321-365 (1984)]. Such diffusion chambers comprise at least one semi-permeable membrane whose pore size (diameter of the aperture or hole) and porosity (total void volume) will vary with the intended application. Well described and commercially available porous membrane filters composed of various compositions including acrylic resins, cellulose-acetate, cellulose-nitrate, nylon, polycarbonate, and other mixed esters fibers are commonly employed. Such semi-permeable membranes form at least one wall of the diffusion chamber and are sealed (by adhesives, heat, ultrasound, and the like), into the diffusion chamber construction in a leak proof manner. The formed diffusion chamber can take a wide variety of different shapes and orientations and will be constructed with an internal volume to meet the requirements of the intended application. With embodiments intended for human use, it is desirable that the internal volume of the diffusion chamber be from 10-200 cubic centimeters and that the effective diffusion distance be not greater than 1.0 millimeters. It is expected that prior to in-vivo implantation or extracorporeal use, the formed chamber will be sterilized using ethylene oxide, gamma radiation, or other conventional non-destructive techniques.

The essence and unexpected therapeutic benefits provided by the methods of the present invention lie in the selection and use of the non-antibody producing leukocytes suspended within the internal volume of a sealed diffusion chamber. Clearly, the semi-permeable membrane of the sealed diffusion chamber will retain the leukocyte suspension internally within the interior of the diffusion chamber while allowing non-cellular materials and fluids to pass therethrough. In this manner, nutrients, salts, and body fluids can pass through the membrane into the interior of the chamber for reaction with the leukocyte suspension while the soluble secretory products released by the leukocyte suspension may flow out from the diffusion chamber into the body of the afflicted subject. The requirements for the semi-permeable membrane are to act as a physical barrier to retain the leukocyte suspension within the interior of the diffusion chamber while allowing non-cellular materials and products to pass unhindered; and to prevent antibodies of the host from penetrating the interior of the chamber and destroying the donor leukocytes. So long as these requirements are met and satisfied, neither the chemical composition of the semi-permeable membrane; nor the pore size of the membrane; nor the porosity of the membrane employed, is of any consequence.

The nature or composition of the cells comprising the leukocyte suspension sealed within the diffusion chamber is thus of paramount interest. Initial experiments have demonstrated, as will be described hereinafter, that a mixture of immunologically normal and functional white blood cells of the types and in the proportional ratios similar to that of white blood cells circulating in the body of normal individuals is both operative and functional as a therapeutic treatment and as a preventative measure of human disease conditions known or believed to involve immune system abnormalities. For humans, such a leukocyte mixture comprises: 36-66% neutrophils; 24-44% lymphocytes; 2-8% monocytes; 1-3% eosinophils; and 0-3% basophils.

A preferred alternative leukocyte mixture will comprise a blend of unselected T-cell lymphocytes obtained from an immunologically normal donor. T-cells may be separated from B cells using conventional methods. The entire T-cell lymphocyte population would then be prepared as a suspension in saline, physiological buffer, or a supportive nutrient medium and be introduced into the interior of the diffusion chamber for use. This T-cell lymphocyte population is unselected in that no ratios or specific subpopulations of T-cells have been identified or purposely included within the suspension. Such mixtures of unselected T-cells will provide a wide variety of immunofunctional T-cell lymphocytes of varying characteristics and antigenic specificities which will then interact as individual cells and subsequently release active secretory products such as various lymphokines into the fluid suspension medium. Such secretory products will pass unhindered through the semi-permeable membrane directly into the tissues and cells of the afflicted individual.

Another embodiment expected to be useful are specific T-cell lymphocyte subpopulations which have been identified by specific antisera and whose relative concentrations or ratios are controlled to be within predetermined limits. In this embodiment, the leukocyte suspension comprises prechosen concentrations of known T-cell subpopulations which are blended together according to a prearranged formula of ratio concentrations to provide an enriched or enhanced concentration of specifically desired T-cell subpopulations. It is expected that enriched concentrations of T4 helper/inducer cells and T8 suppressor/cytotoxic cells will dominate such enriched T-cell leukocyte suspensions. In addition, as further information regarding additional T-cell subpopulations (there now being approximately 19 identifiable T-cell subpopulations) are found and as new immunological and cellular functions are recognized for each specific T-cell subpopulation, that the choice of T-cell subpopulation types and the respective concentrations of each within the leukocyte suspension will be altered to meet specific immunological disorders and disease states. All such variations in T-cell subpopulation selection, ratio of subpopulation concentration, and mode of interaction between different specific T-cell subpopulations, are deemed to be within the scope of the leukocyte suspensions generally useful within the present invention.

Another expected embodiment of the leukocyte suspension will utilize specific T-cell subpopulations which are maintained as individual cell lines and cloned using conventionally known techniques to provide a pure strain of cells. Clones of specific T-cell subpopulations allow the user to maintain individual cell lines of uniform characteristics; of known antigenic specificity; having established receptor sites on the cell surface; and having proven ability to interact with other specific T-cell subpopulations when in admixture. This provides the user with an added degree of choice and control in blending specific T-cells of desired characteristics and in making a leukocyte suspension for use within the diffusion chamber such that specific secretory products can be expected to be synthesized in advance by virtue of having combined specific T-cell clones.

Regardless of the precise composition of the leukocytes employed in the suspension, the present invention relies on the interaction of these cells and the ability of these cells to release secretory products into the fluid suspension medium. It is the release of such lymphokines and other soluble cell products which act as the therapeutic agents in counterbalancing the effects of the immunological disorder or disease and which aid in preventing further injury to the cells and tissues of the afflicted individual. There is no information available at this time to describe the true mechanism of action by which the release of such cytokines or other secretory products act as chemical mediators in-vivo. Interleukins and Interferons are only two examples of this rapidly expanding class of mediator molecules. The invention, however, relies on the release of at least one distinct secretory product, usually in soluble form, which is the result of infrinsic leukocyte activity or leukocyte interaction within the diffusion chamber. The released secretory products will then pass through the semi-permeable membrane of the diffusion chamber and in this manner, be physiologically released into the body of the subject. Such secretory products transfusions are effective not only in treating clinically identifiable diseases such as diabetes, but also in restoring much of the original function to the immunodeficient white blood cells circulating within the afflicted subject. The sealed diffusion chamber, whether surgically implanted or attached as an extracorporeal device, acts as the means for compartmentalizing the prepared leukocyte suspension and physically separates them from their host counterparts. The semi-permeable membranes allow the host to provide fluids and nutritional materials necessary for cell growth while preventing direct donor-recipient cell to cell interaction. These in-vivo methods thus provide means for therapeutically treating immunological defects and abnormalities under physiological conditions in a manner which does not further the progression of the disorder/disease and allows for continuous action of the donor cells for indefinite periods of time. It will be recognized, that by segregating the leukocyte suspension to the interior of the sealed diffusion chamber, the histocompatibility of the donor cells (with relation to the host recipient) becomes immaterial and inconsequential; moreover, because it is solely the secretory products of activated normal leukocytes which act on the affected cells and tissues of the recipient, there are no undesired reactions, new antibodies, or any other immune response by the host's cells and tissues. It will be recognized also, especially in the extracorporeal embodiments of the present invention, that the donor cells can be replaced as frequently as desired with or without a preset schedule; similarly, the implanted diffusion chambers may be removed without major injury or discomfort to the host.

Some preferred embodiments of the present invention utilize a semi-permeable membrane as a sealable diffusion chamber without need for any other material or housing construction. Such sealable diffusion chambers comprise semi-permeable hollow fibers composed of polysulfone or acrylic copolymer which have an internal diameter ranging from about 300–2,000 micrometers (hereinafter "um"), are approximately 4–7 centimeters long, and whose membranes have a wall thickness ranging from about 50–110 um. Such fibers are useful individually and as part of the artificial capillary systems (Vitafiber), manufactured and sold by Amicon Corporation. The pore size of such hollow fiber, semi-permeable membranes will retain molecules ranging between about 10,000–100,000 daltons. For most purposes, hollow fiber membranes with a mean pore size of 70 Angstroms (corresponding to a cut-off of approximately 80,000 daltons) have been found useful in most instances. When the lumen of these hollow fibers are filled with leukocytes from the immune system of normal donor individuals and the ends of these tubes are subsequently sealed, a passive diffusion chamber is formed. The physical characteristics of the sealed hollow fiber, semi-permeable membranes assures that nutrients can diffuse freely into the interior of the hollow fiber; that the leukocytes within the internal volume of the chambers are protected from destruction by host cells and host immunoglobulins; and that the secretory products released by the cells within the hollow fibers diffusion chamber can diffuse into the host tissues. These hollow fiber membranes have been shown to be well tolerated in-vivo and to be non-toxic after implantation in living recipients.

Figure 1:
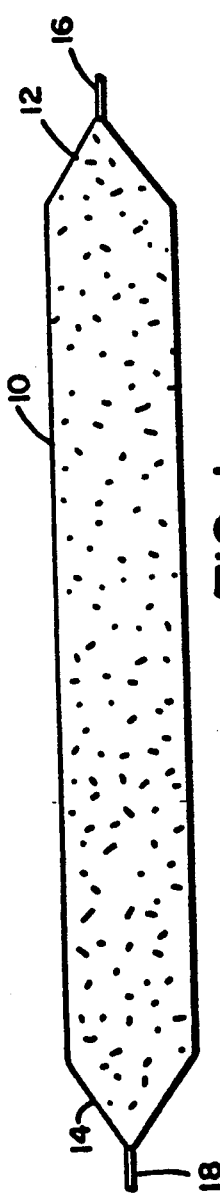
FIG. 1 is an overhead view of one preferred embodiment of the present invention.

The preferred embodiment of the sealed diffusion chamber employing such hollow fiber membranes is illustrated by FIGS. 1 and 2 respectively. As seen therein, a semi-permeable membrane formed in the shape of a hollow fiber tube 10 appears whose ends 12, 14 are tapered and sealed (preferably by heat or ultrasonic welding). The seals 16, 18 ensure that the leukocyte suspension 20 remains within the lumen 8 of the hollow fiber 10. The embodiment illustrated by FIGS. 1 and 2 respectively is particularly useful for surgical implantation in-vivo, especially at a subcutaneous site.

Figure 4:
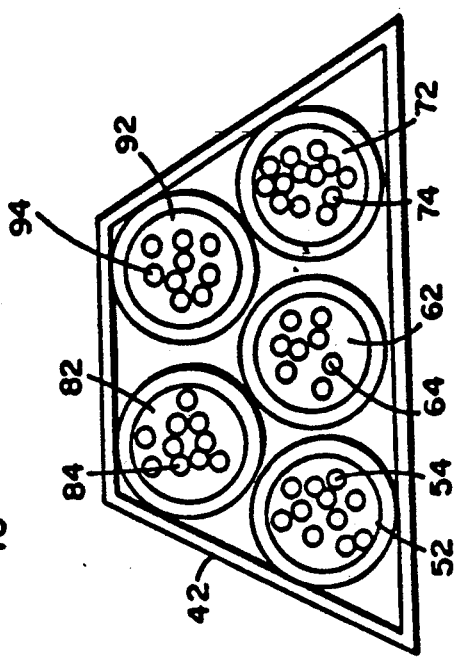
FIG. 4 is a cross-sectional view of the embodiment illustrated within FIG. 3.
Figure 3:
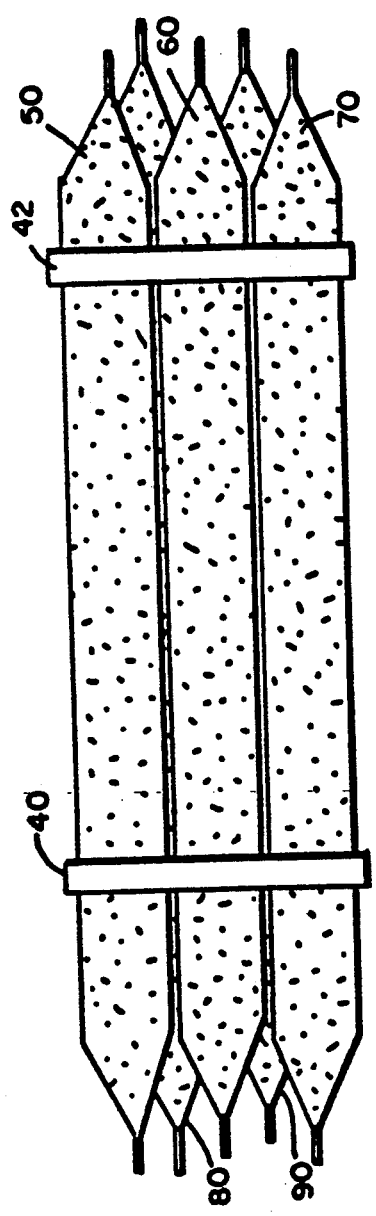
FIG. 3 is a overhead view of a plurality of sealed diffusion chambers joined together as a unit for implantation in-vivo.

Another embodiment is illustrated by FIGS. 3 and 4 respectively. As seen therein, a plurality of sealed semi-permeable hollow fibers 50, 60, 70, 80, and 90 respectively are joined together by a pair of restraints 40, 42 to form a bundle. Within the lumen of each sealed hollow fiber tube 52, 62, 72, 82, and 92, are a series of leukocyte suspensions 54, 64, 74, 84, and 94 respectively. The prepared bundle may be implanted using standard surgical procedures at any preselected site in a recipient host.

Figure 5:
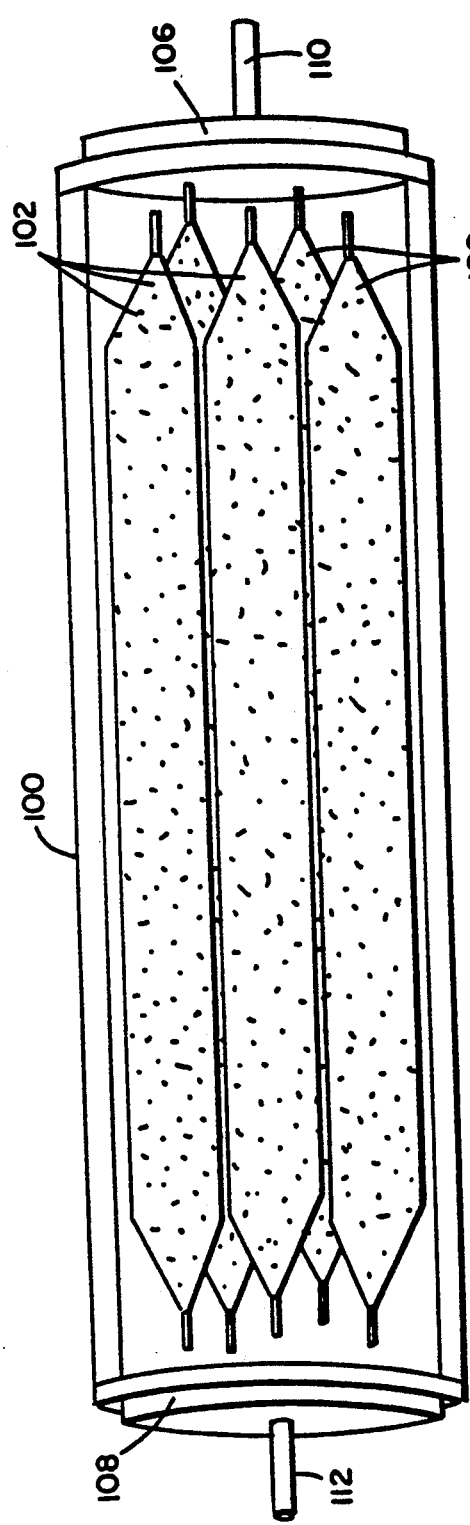
FIG. 5 is an overhead view of an active diffusion chamber suitable for implantation in-vivo with a blood vessel of the subject.
Figure 6:
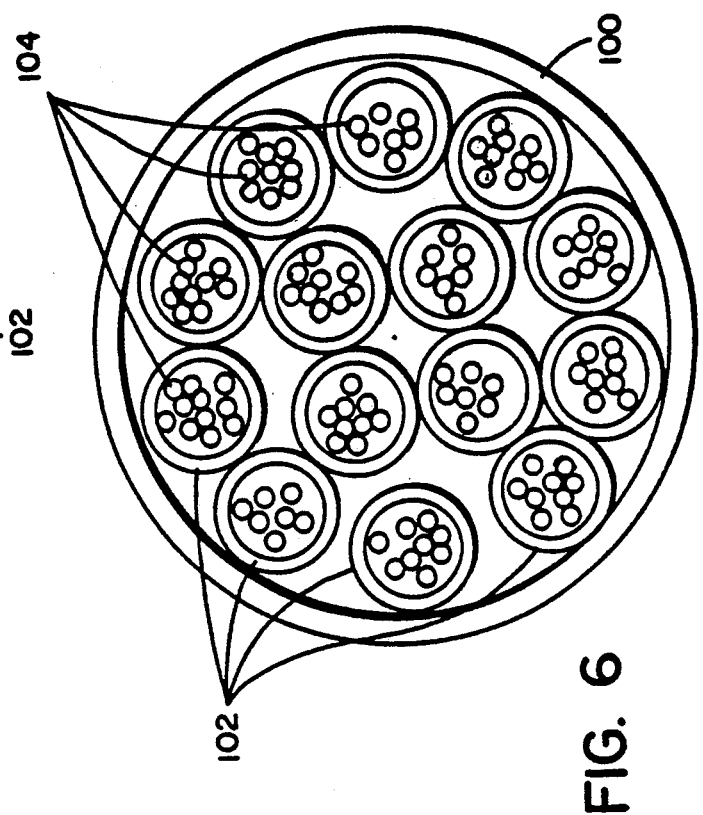
FIG. 6 is a cross-sectional view of the embodiment illustrated by FIG. 5.

It is envisioned that under specific circumstances, the rate at which the secretory products are released from the leukocyte suspension within a sealed diffusion chamber may be too slow to provide effective therapy. Such passive diffusion chambers rely on concentration gradients, natural diffusion, and the passive flow of fluids into and out of the diffusion chamber to transport the released secretory products to the areas in the host's body where they will be therapeutically effective. For more rapid release and active distribution of secretory products directly into the circulatory system of the afflicted individual, the embodiment illustrated by FIGS. 5 and 6 is preferred. As seen therein, a cylindrically shaped culture tube 100 formed of a biocompatible, non-toxic material houses a plurality of individually sealed diffusion chambers 102. Sealed within each of these hollow fiber diffusion chambers is a leukocyte suspension 104 able to interact and to release cellular secretory products. Each end of the tube 100 is enclosed by a tubing connector 106, 108 and from which extends a blood vessel attachment support 110, 112. This embodiment is intended to be surgically implanted into a blood vessel. The selected blood vessel is surgically severed and each end is attached to a support 110, 112 directly such that the blood exiting the vessel enters the interior of the culture tube 100 and bathes the plurality of semi-permeable diffusion chambers 102. The pressure within the blood vessel will cause a partial pressure and fluid flow axially through the culture tube 100 such that the secretory products released by the leukocyte suspension within the fibers 102 become rapidly transported by the blood fluid passing through the semi-porous membrane material and flowing out of the culture tube 100 back into the host's circulatory system. While the blood circulatory system is preferred as the site of implantation, it is recognized that the active diffusion chamber illustrated by FIGS. 6 and 7 may also be placed within the lymphatic fluid system of the individual to achieve equivalent effects.

Figure 7:
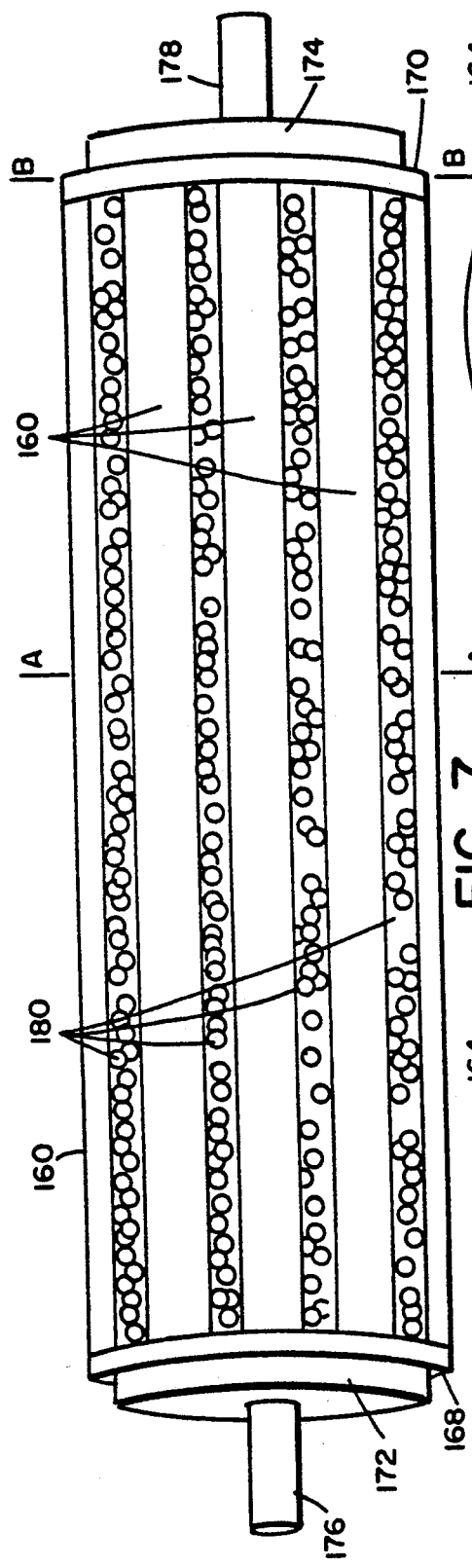
FIG. 7 is an overhead view of a preferred embodiment of an active diffusion chamber useful as an implant with a blood vessel off the subject.
Figure 8B:
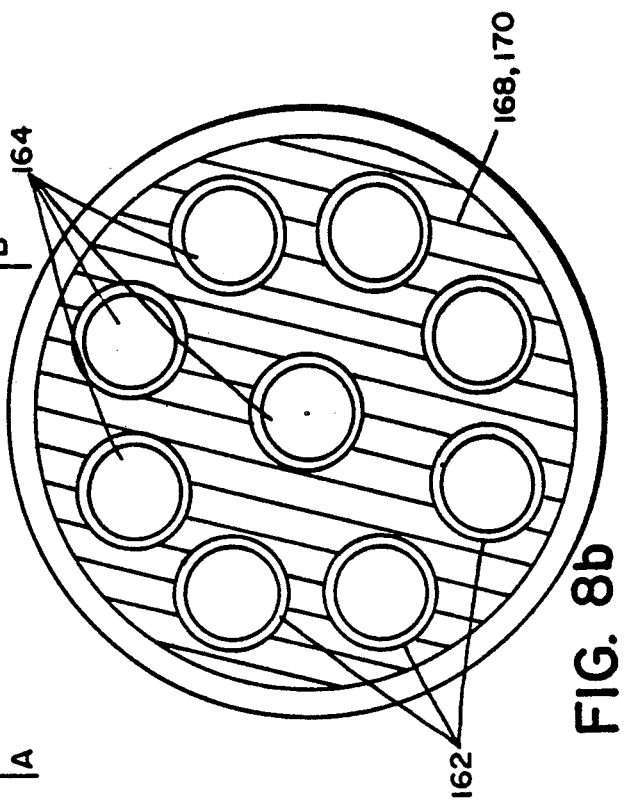
FIG. 8a and 8b are cross-sectional views of the embodiment illustrated by FIG. 7.
Figure 8A:
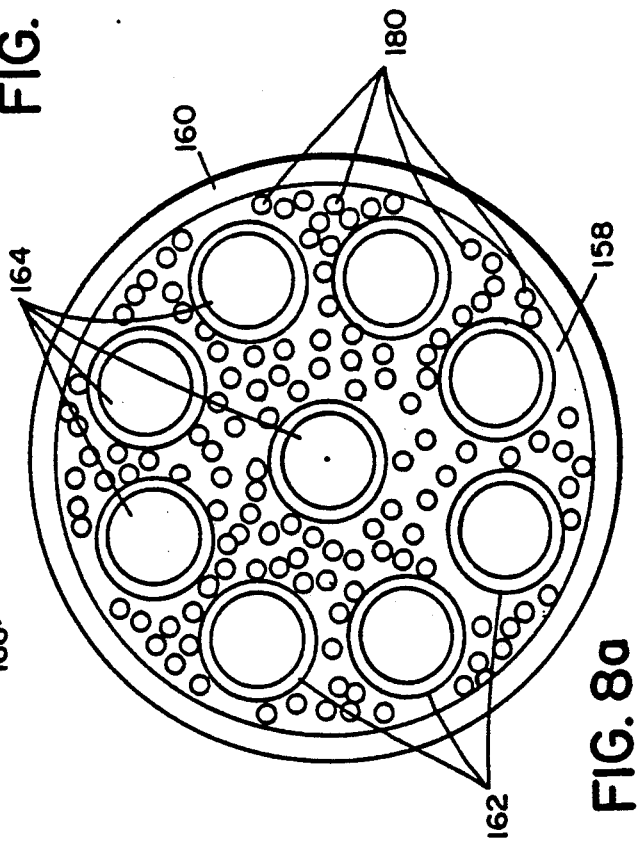

A preferred format for the active diffusion chamber to be positioned in-line with a blood vessel for rapid distribution of released secretory products is the embodiment illustrated by FIGS. 7, 8a and 8b respectively. FIG. 8a is a cross-sectional view along the line AA of FIG. 7; FIG. 8b is a cross-sectional view along the line BB of FIG. 7. This embodiment is most desirable because this format maintains the linear blood flow of the blood uniformly throughout the entirety of the diffusion chamber from end to end. This allows the blood pressure of the system to be kept near its original level and avoids the risk of subsequent complications in the body typically caused by interruptions of laminar blood flow.

As seen in FIGS. 7, 8a and 8b, a cylindrical shaped tube 160 houses a plurality of axially positioned hollow fiber membranes 162 which are individually joined and sealed fluid-tight to individual aperatures 166 in circular support plates 168, 170 positioned at each end of the tube 160. The integrity of the lumen 164 of each hollow fiber membrane within the tube 160 is maintained and each lumen serves as a fluid pathway for the blood through the interior of the tube 160. At each end of the tube is a filling chamber 172, 174, each of which includes a blood vessel attachment 176, 178. Filling the interior 158 of the tube 160 and surrounding the external surfaces of the axially positioned hollow fiber membranes 162 is a prepared leukocyte suspension 180. In the normal course of use, blood exiting the blood vessel joined to the attachment 176 enters the filling chamber 172 and is confronted by the support plate 168 presenting the open ends and lumen of the hollow fiber membranes 162. The blood enters the lumen 164 of each hollow fiber membrane 162 through the aperatures 166 in the support plate 168. The blood then flows through the length of the axially positioned membranes 162 within the interior 158 of the tube 160 to the other support plate 170. The secretory products synthesized and released by the leukocyte suspension 180 within the interior 158 of the tube 160 flow into the hollow fibers 162 and are transported by the blood flowing tangentially through the lumen of the fiber membranes. The blood pressure is maintained through the entirety of the tube 160 and the blood exits the diffusion chamber through the aperatures 166 of the support plate 170 into the filling chamber 174 and re-enters the blood vessel via the attachment 178.

Figure 9:
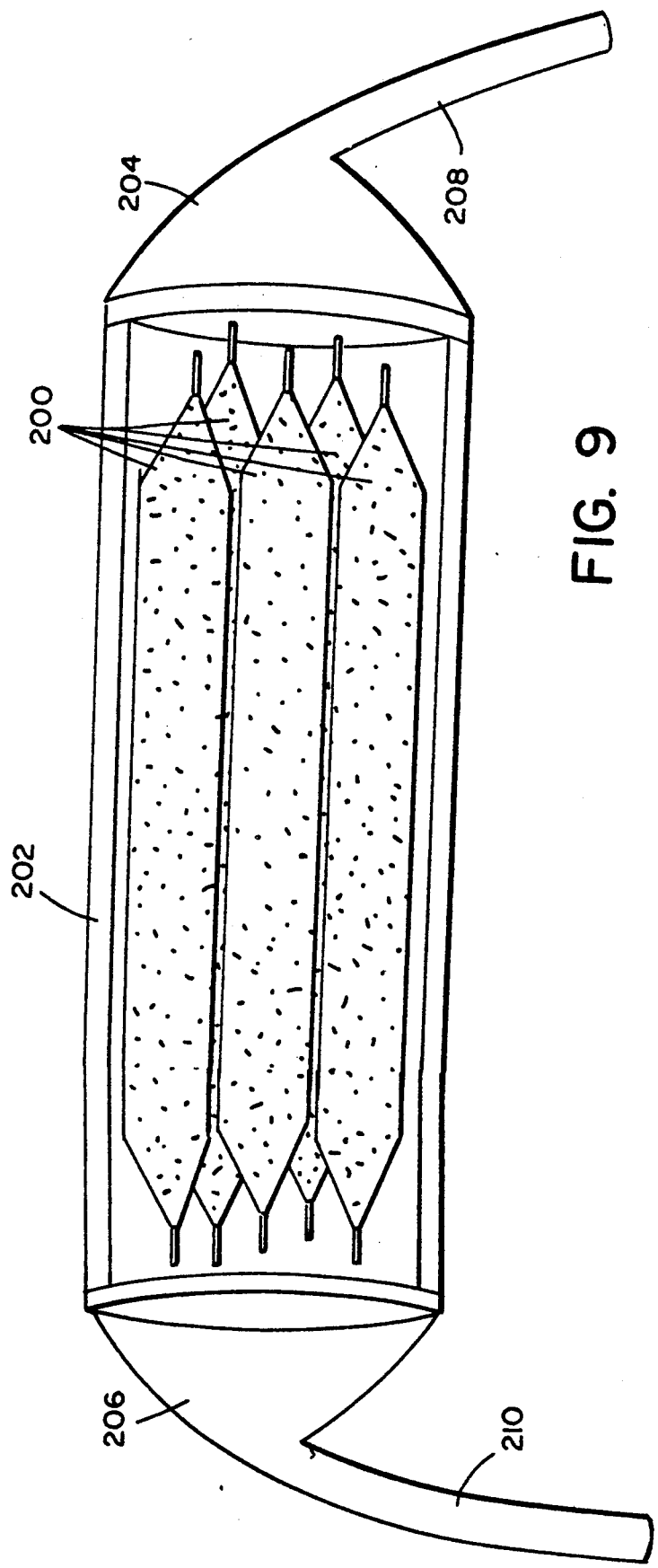
FIG. 9 is an overhead view of an extracorporeal embodiment of the present invention intended to be externally joined to the circulatory system of the subject.

The extracorporeal form of the apparatus used in the present methodology is illustrated by FIG. 9, or alternatively by FIG. 7. The extracorporeal embodiment is intended to be used when there is a recognized causative agent active and present within the afflicted individual at the time therapeutic treatment is initiated. Such a situation is the AIDS patient. As illustrated by FIG. 9, a plurality of sealed hollow fiber semi-permeable membranes serving as diffusion chambers 200 is contained within a cylindrically shaped housing 202. At each end of the housing 202, is a catheter closure 204, 06, each of which terminates as a catheter 208, 210 for direct connection to the circulatory system of the afflicted individual. This extracorporeal diffusion chamber utilizes the blood pressure of the recipient to propel fluid through a catheter 208 into the interior of the housing 202 and to bathe the leukocyte suspensions within the sealed diffusion chambers 200. The pressurized fluid flow will actively remove released secretory products of the leukocyte suspension from within the diffusion chambers 200 and cause them to flow through the end 206 and the return catheter 210 into the blood system of the recipient. In this manner, the release secretory products produced within the sealed diffusion chambers are actively removed and transported from within the chamber housing at a rate far greater than that provided by passive diffusion and other passive transfer mechanisms.

To document the utility and the effectiveness of the methodology and apparatus comprising the present invention, the following experiment is provided. It will be expressly understood and recognized, however, that the experimental design, clinical condition, test parameters, leukocyte mixture, and described mode of use is not limiting or restrictive of the invention in any manner.

The BB/W rat develops spontaneous autoimmune diabetes which is characterized by many metabolic, pathologic, and immunological features similar to those observed in human insulin dependent diabetes mellitus [Rossini et al., *Ann. Rev. Immunol.* 3:289–320 (1985); Yale and Marliss, *Clin. Exp. Immunol.* 57:1–20 (1984)]. These rats are of normal body weight, and both sexes are equally susceptible. At the time of disease onset, diabetic ketoacidosis invariably occurs and is lethal unless treated with insulin. Daily insulin injections are needed to keep affected rats alive. The disorder appears not to be the result of an infection, and no environmental factors that consistently affect the incidence of diabetes have yet been described.

While the etiology of BB rat diabetes is presently unknown, abnormalities of cellular immunity are well documented. Mitogen stimulated spleen cells from acutely diabetic rats adoptively transfer both insulitis and diabetes to various recipient rats. Marked lymphopenia involving all lymphocyte subsets occurs consistently in the BB rat. Activated T-lymphocytes have been reported to occur during the early stages of diabetes and to decrease with time. The responsiveness of BB lymphocytes to mitogens is defective and lymphocytic thyroiditis also occurs in these rats. Lastly, it has been demonstrated that islets from resistant BB rats transplanted to spontaneously diabetic rats are rapidly destroyed.

A series of sealed diffusion chambers containing a mixed leukocyte suspension comprising spleen cells from normal Wistar Furth rats were prepared. Wistar Furth (WF) rats never become diabetic. Semi-permeable hollow fibers which are inner-sponge, and have an outer skin membrane with a mean pore size of 70 Angstroms (which corresponds to approximately 80,000 daltons in molecular weight) were utilized. These hollow fiber semi-permeable membranes were obtained from the Amicon Division of W. R. Grace, Inc. (Lexington, Mass.). These hollow fibers have approximately 1,000 um diameters and a length of approximately 5.0 centimeters.

The leukocyte suspension comprised spleen cells from normal WF rats suspended in supplemented RPMI medium by mechanical dispersion as described in Rossini et al., *J. Clin. Invest.* 74:39–44 (1984). In brief, WF donor rats of both sexes and various ages were killed.

The spleens were removed by sterile technique and mechanically disrupted with an autoclaved garlic pressed. Extruded cells were collected in 10 ml of RPMI medium and the volume of the suspension increased to 45 ml with additional RPMI medium. Subsequently, the cells were centrifuged at 1200×gravity for 10 minutes; washed with saline; and the cells resuspended in RPMI. The cells were then used directly when freshly prepared or first cultured for 72 hours with a mitogen, concavalin A (hereinafter "Con A", 5 ug/ml). Subsequently, a cell suspension of 100–150×10$^6$ cells/milliliter was introduced into the lumen of each hollow fiber by capillary action and the diffusion chamber sealed by joining each end with Amicon solvent. 5.0 centimeter approximately length tubes were utilized for ease of handling and maximum length for easy positioning internally within 30 day old BB rats. Each recipient BB rat received four individual fibers or diffusion chambers implanted into the peritoneal cavity by conventional surgical techniques. 29 BB rats received CON A activated spleen cells within the respective diffusion chambers while 10 BB rats received fresh (non-stimulated, non-cultured) spleen cells within their respective diffusion chambers. 11 control BB rat recipients received untreated, empty hollow fibers. In addition, 40 BB rats received no treatment whatsoever, but were evaluated as 19 negative controls. All the rats were clinically tested for evidence of diabetes through 120 days of age. It is recognized that selective beta cell destruction and clinical diabetes occurs by 120 days of age in about one-half of all BB rats. The results are presented by Table I below.

TABLE I

| RAT GROUP AND CONDITION | NUMBER TESTED | NUMBER OF DIABETIC RATS | % DIABETIC RATS |
|---|---|---|---|
| CON A Activated WF Spleen Cells | 29 | 1 | 3 |
| Fresh, Untreated WF Spleen Cells | 10 | 1 | 10 |
| Empty Chamber | 11 | 6 | 55 |
| No Treatment | 40 | 19 | 48 |

This experiment clearly indicates that the secretory products released by the leukocyte suspension contained within the hollow fiber diffusion chambers can prevent the onset of clinical diabetes. It is the release of these secretory products such as soluble factors or other lymphokines which accounts for the protection and for the counterbalancing effect. The sealed diffusion chamber, however, is not subject to either specific or non-specific host defenses and provides much greater protection over an enduring period of time than can be accomplished by direct transfer of white blood cells from the donor into the circulation of the afflicted subject.

The invention is not to be restricted in form nor limited in scope except by the claims appended hereto.

What we claim is:

1. An in-situ immunological method for therapeutically treating disorders and disease states which are characterized by the presence of immunologically abnormal leukocytes in the body of an afflicted subject, said method comprising the steps of:

obtaining a sealed diffusion chamber of definable configuration and internal volume, said diffusion chamber comprising at least one semi-permeable membrane and at least a suspension of viable, immunologically normal, T-cell keukocytes, said semi-permeable membrane retaining said normal, T-cell leukocyte suspension within said diffusion chamber while allowing non-cellular materials and fluids to pass therethrough, said T-cell keukocytes in said suspension being demonstratably able to provide normal T-cell functions and to produce normal, non-antibody, T-cell secretory products within said diffusion chamber;

implanting said sealed diffusion chamber at a preselected site within the afflicted subject; and allowing the non-cellular materials and fluids of the afflicted subject to pass through said semi-permeable membrane and to interact with said normal T-cell keukocyte suspension within said implanted diffusion chamber, said interaction yielding an in-situ production and release of normal, non-antibody, T-cell secretory products from said leukocyte suspension sufficient to therapeutically treat the immunological abnormality of the afflicted subject.

2. The method as recited in claim 1 wherein said leukocyte suspension comprises mixed circulating white blood cells.

3. The method as recited in claim 1 wherein said leukocyte suspension comprises unselected T-cells.

4. The method as recited in claim 1 wherein said leukocyte suspension comprises specific T-cell subpopulations.

5. The method as recited in claim 1 wherein said leukocyte suspension comprises cloned T-cells.

6. An in-situ immunological method for treating diabetes, comprising:

obtaining a sealed diffusion chamber of definable configuration and internal volume, said diffusion chamber comprising at least one semi-permeable membrane and at least a suspension of viable, immunologically normal, T-cell leukocytes, said semi-permeable membrane retaining said normal, T-cell leukocyte suspension within said diffusion chamber while allowing non-cellular materials and fluids to pass therethrough, said T-cell leukocytes in said suspension being demonstrably able to provide normal T-cell functions and to produce normal, non-antibody, T-cell secretory products within said diffusion chamber;

implanting said sealed diffusion chamber at a preselected site within the afflicted subject; and allowing the non-cellular materials and fluids of the afflicted subject to pass through said semi-permeable membrane and to interact with said normal T-cell leukocyte suspension within said implanted diffusion chamber, said interaction yielding an in-situ production and release of normal, non-antibody, T-cell secretory products from said leukocyte suspension sufficient to therapeutically treat the immunological abnormality of the afflicted subject.

7. An implantable immunological article for therapeutic treatment of disorders and disease states which are characterized by the presence of immunologically abnormal leukocytes in the body of an afflicted subject, said article comprising:

a sealed diffusion chamber of definable configuration and internal volume, said diffusion chamber comprising at least one hollow-fiber semi-permeable membrane able to retain at least a suspension of viable, immunologically normal, T-cell keukocytes within said internal volume of said chamber while allowing non-cellular materials and fluids to pass therethrough; and at least a suspension of viable, immunologically normal T-cell leukocytes within said sealed diffusion chamber, said T-cell leukocytes being non-antibody producing cell demonstrably able to provide normal T-cell functions and to produce normal, non-antibody, T-cell secretory products within the non-cellular materials and fluids of the afflicted subject sufficient to therapeutically treat the immunological abnormality after implantation of said sealed diffusion chamber at a preselected site within the afflicted subject.

8. The implantable article as recited in claim 7 further comprising a plurality of said sealed diffusion chambers.

9. The article as recited in claim 7 wherein said leukocyte suspension comprises a mixture of circulating white blood cells.

10. The article as recited in claim 7 wherein said leukocyte suspension comprises unselected T-cells.

11. The article as recited in claim 7 wherein said leukocyte suspension comprises specific T-cell subpopulations.

12. The article as recited in claim 7 wherein said leukocyte suspension comprises cloned T-cells.

* * * * *

UNITED STATES PATENT AND TRADEMARK OFFICE
CERTIFICATE OF CORRECTION

PATENT NO. : 5,026,365

DATED : June 25, 1991

INVENTOR(S) : Aldo A. Rossini, John P. Mordes and Eugene S. Handler

It is certified that error appears in the above-identified patent and that said Letters Patent is hereby corrected as shown below:

Claim 1, column 13, line 65, change "keukocytes," to ---leukocytes,---

Claim 1, column 14, line 1, change "keukocytes" to ---leukocytes---

Claim 1, column 14, line 11, change "keukocyte" to ---leukocyte---

Claim 7, column 14, line 65, change "keukocytes" to ---leukocytes---

Signed and Sealed this

Tenth Day of November, 1992

*Attest:*

DOUGLAS B. COMER

*Attesting Officer*  Acting Commissioner of Patents and Trademarks

UNITED STATES PATENT AND TRADEMARK OFFICE
CERTIFICATE OF CORRECTION

PATENT NO. : 5,026,365
DATED : June 25, 1991
INVENTOR(S) : Aldo A. Rossini, et. al.

It is certified that error appears in the above-indentified patent and that said Letters Patent is hereby corrected as shown below:

Column 1, line 5, insert --<u>Government Support</u>:

This inventon was made with government support under grant number DK-25306, awarded by the National Institutes of Health. The government has certain rights in the invention--.

Signed and Sealed this

Seventh Day of June, 1994

Attest:

BRUCE LEHMAN

Attesting Officer

Commissioner of Patents and Trademarks